United States Patent [19]

Hori et al.

[11] Patent Number: 4,995,731
[45] Date of Patent: Feb. 26, 1991

[54] METHOD FOR MEASURING HEAT TRANSFER COEFFICIENT AND SENSOR INCLUDING HEAT TRANSFER ELEMENT AND THERMAL INSULATION ELEMENT

[75] Inventors: Tomoshige Hori, Kitamoto; Kensuke Itoh, Kodaira, both of Japan

[73] Assignee: Snow Brand Milk Products Co., Ltd., Japan

[21] Appl. No.: 157,260

[22] Filed: Feb. 18, 1988

[30] Foreign Application Priority Data

Mar. 3, 1987 [JP] Japan .................................. 62-48566
Mar. 4, 1987 [JP] Japan .................................. 62-49372

[51] Int. Cl.$^5$ ........................................... G01N 25/20
[52] U.S. Cl. ...................................... 374/43; 374/29; 374/185; 374/31; 374/44; 338/25
[58] Field of Search ..................... 374/43, 44, 29, 31, 374/185; 338/25

[56] References Cited

U.S. PATENT DOCUMENTS

| | | | |
|---|---|---|---|
| 2,878,669 | 3/1955 | Knudson et al. | 374/44 |
| 2,994,818 | 9/1959 | Harman | 374/43 |
| 3,266,290 | 3/1964 | Haacke | 374/44 |
| 3,317,822 | 1/1963 | Watson | 374/43 |
| 4,563,096 | 1/1986 | Katafuchi | 374/43 |
| 4,578,988 | 4/1986 | Hori et al. | 374/43 |

FOREIGN PATENT DOCUMENTS

| | | | |
|---|---|---|---|
| 0149242 | 1/1962 | U.S.S.R. | 374/43 |
| 2131175 | 6/1984 | United Kingdom | 374/43 |

OTHER PUBLICATIONS

Parsons, Jr. et al., *Measurement of Properties of Liquids and Gases Using a Hot-Wire Technique*, in Rev. Sci. Instr. 49 (10), pp. 1460-1463, Oct. 1978.

*Primary Examiner*—William A. Cuchlinski, Jr.
*Assistant Examiner*—Diego F. F. Gutierrez
*Attorney, Agent, or Firm*—Griffin, Branigan & Butler

[57] ABSTRACT

A method for measuring a heat transfer coefficient between a heat transfer element and a fluid comprising a measurement of a calorific value by placing the heat transfer element into the fluid and charing the heat transfer element with electricity. A calorific value of a particular surface of the heat transfer element is the true calorific value of the entire heat transfer element, since the particular surface of the heat transfer element is thermally insulated from a residual surface of the heat transfer element so as to prevent a heat transfer of the residual surface of the heat transfer element.

7 Claims, 3 Drawing Sheets

GENERAL PURPOSE INTERFACE BUS

METHOD FOR MEASURING HEAT TRANSFER COEFFICIENT AND SENSOR INCLUDING HEAT TRANSFER ELEMENT AND THERMAL INSULATION ELEMENT

BACKGROUND OF THE INVENTION

The present invention generally relates to a method for measuring a heat transfer coefficient which is necessary to measure in order to determine the properties of many kinds of fluid by the so-called electrical heating method. The present invention also relates to a sensor which can measure a heat transfer coefficient by a heat transfer element.

The term "fluid" as used in the present invention includes not only a liquid substance and a gaseous substance but also a semi-solid substance, namely a substance which can flow.

Generally, it is very important for a process controll of a fluid to measure properties of the fluid (for example kinematic viscosity).

In Japanese Patent laid-open application No. 60 (1985)-152,943, there is disclosed a method for measuring properties of a fluid by using a thin metal wire as a heat transfer element by putting the thin metal wire into a fluid as a measuring object, charging the thin metal wire with electricity so as to the heat transfer element and then calculating a heat transfer coefficient on the surface of the thin metal wire.

The abovementioned method is well known as shown in FIG. 6. That is to say, a conduction lead wire 2—2 and a voltage measuring lead wire 3—3 are connected at the two ends of a thin metal wire 1 which is a heat transfer element made of a heating material. An electric current is sent into the thin metal wire 1 through the conduction lead wire 2—2 and the voltage applied to the thin metal wire 1 is measured by a volt meter 4 connected with the voltage measuring lead wire 3—3. According to the relation of the voltage V measured by the volt meter 4 to the electric current I of the thin metal wire 1, a electrical resistance R is calculated and further a calorific value W is calculated by the following formula (1)

$$W = I^2 R \qquad (1)$$

A heat transfer coefficient $\alpha$ at the boundary surface between the thin metal wire and the fluid is calculated by using the calorific value W and the following formula (2)

$$\alpha = w'd/4 \, (\theta_s - \theta_\infty) \qquad (2)$$

d: diameter of thin wire
w': W/v (volume of thin wire)
$\theta_s$: surface temperature of thin wire
$\theta_\infty$: temperature of fluid A kinematic viscosity is calculated by the heat transfer coefficient $\alpha$ according as the well-known relational expression which, for example, appears in the Japanese reference (Japan Food Industry Academy Review, 1988 vol. 1 § the introduction.

In the abovementioned method for measuring a heat transfer coefficient of a fluid, the heat being transferred in a non-radial direction from the two ends 5, 5 will be unknown. However, when the heat transfer element is made of a thin wire (a ratio of diameter to length of the thin wire is about <1:1000), the heat loss abovementioned from the two ends 5, 5 becomes extremely small as compared with that lost from the circumferential surface of the thin metal wire 1. Therefore, when disregarding the heat capacity lost from the two ends 5, 5 and regarding the heat capacity W of the whole heat transfer element as a heat capacity escaping to the fluid from the circumferential surface, the measurment error thereof is small.

However, when it is desired to miniaturize the heat transfer element, the heat transfer coefficient between the heat transfer element and a measuring object cannot be exactly judged. That is a new problem to be solved.

That is to say, as shown in FIG. 7, when a metal stick 6, formed by shortening the thin wire, is used as a heat transfer element and the circumferential surface 7 thereof is contacted with a fluid as the measuring object, in the abovementioned method for measuring the heat transfer coefficient, the desired heat capacity is a heat capacity transfered between the heat transfer element and the measuring object, namely, it corresponds to a heat capacity $W_1$ escaped from the surface 7 of the metal stick to the fluid.

However, in a miniaturized heat transfer element, the heat generated from the heat transfer element 6 also escapes from the two end surfaces 8, 8 of the heat transfer element 6 as shown in the figure. When a heat capacity lost from the two end surfaces 8, 8 is $W_2$, the whole calorific value of the heat transfer element 5 is the sum of the heat capacity $W_2$ and the heat capacity $W_1$ transferring to the fluid.

$$W = W_1 + W_2 \qquad (3)$$

In the miniaturized heat transfer element, the ratio of $W_1/W_2$ is not essentially infinite, which is different from that of the method for measuring a heat transfer coefficient of a fluid by using the long thin metal wire, and the unmeasured heat capacity $W_2$ becomes larger in comparison with the heat capacity $W_1$. The difference thereof cannot be ignored.

Accordingly, in the above case, when regarding the heat capacity W of the whole heat transfer element as the heat transfer element $W_1$ transferring into the surrounding fluid, the heat transfer coefficient cannot be exactly measured because of the error resulting from the assumption that no heat capacity $W_2$ is lost from the two end surfaces 8, 8.

These disadvantage occurs similarly, when using a heat absorption material as a heat transfer element.

SUMMARY OF THE INVENTION

An object of the present invention is to provide a method for measuring a heat transfer coefficient and to provide a sensor, including a heat transfer element and a thermal insulation element, which can precisely and directly measure the true value of a heat transfer coefficient between a heat transfer element and a fluid as a measuring object without any errors, such as those descibed above when the heat transfer element is miniaturized.

According to the present invention, one of these objects is achieved by measuring a calorific value with a heat transfer element placed into the fluid and heating the heat transfer element with electricity, wherein a heat capacity of a particular surface of the heat transfer element can be regarded as the heat capacity of the entire heat transfer element by heat-transferably contacting the particular surface of the heat transfer element with the fluid and making the residual surface of the heat transfer element thermally insulating.

Thus, in the present invention, a heat transferable state is not limited to a state in which the heat transfer element is entirely physically contacted with the fluid to be measured.

In performing the aforesaid method, a sensor is provided, which includes a heat transfer element where a particular surface is heat-transferably contacted with a fluid and a thermal insulation element is heat-transferably contacted with the residual surface of the heat transfer element. The operation of the sensor is such that heat cannot be transferred between the heat transfer element and the thermal insulation element by reason of the holding temperature of the thermal insulation element at a temperature which is substantially equal to the temperature of the interface between the heat transfer element and the thermal insulation element.

It is well-known that heat transfers by a difference of temperature. According to the present invention, since a particular surface of the heat transfer element placed into a fluid as a measuring object is heat-transferably contacted with the fluid and the residual surface of the heat transfer element is thermally insulated, a heat transfer between the heat transfer element and the fluid as a measuring object occurs only at the particular surface of the heat transfer element, i.e. only on that surface where the heat transfer element is heat-transferably contacted with the fluid. Therefore, according to the present invention, if a miniaturization of a heat transfer element is required, a true heat capacity transfered between the heat transfer element and the fluid as a measuring object can be exactly measured without any error and the properties of the fluid can be also precisely measured.

DETAILED DESCRIPTION OF THE INVENTION

Figure 1:
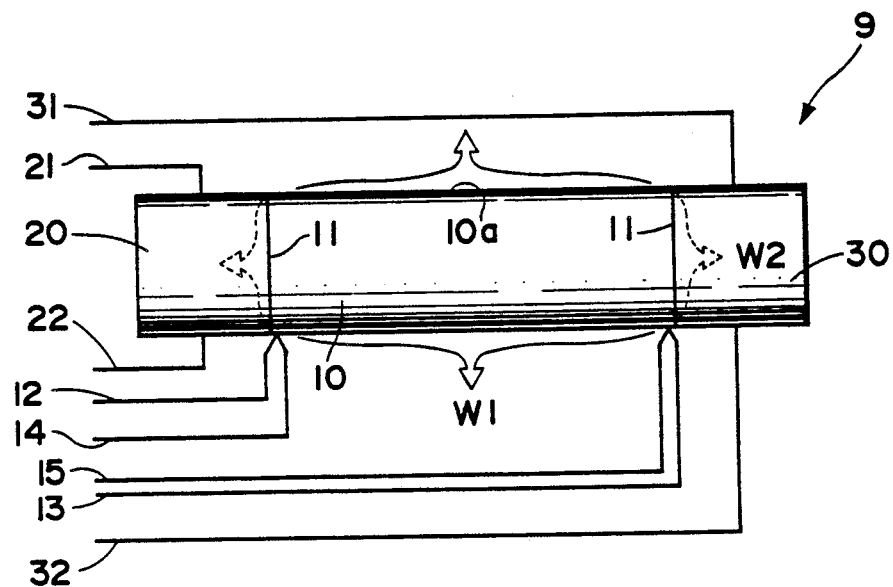
FIG. 1 is a front view illustrating an embodiment in which a combination of a heat transfer element and a thermal insulation element is in the shape of a cylindrical body.

The invention will now be described by way of examples with reference to the accompanying FIGS. 1 to 5.

In the invention, a heating material may be used as the heat transfer element or a heat absorbing material may also be used as a heat transfer element and the usage thereof is the same as that of the examples where a heating material is used as the heat transfer element.

A first embodiment wherein a combination of a heat transfer element and a thermal insulation element in the shape of a cylindrical body is used, will be described with reference to FIGS. 1 and 2. A sensor 9 includes a heat transfer element 10 and thermal insulation elements 20, 30. The heat transfer element is in the shape of a cylindrical body and it is made of a metal having a conductivity and a exothermic ability. Platinum has a small circular change of electrical resistance and is preferably used as the metal. The thermal insulation element 20, 30 are interfaced with the two end sides of the heat transfer element and the thermal insulation element is also made of a metal having exothermic ability.

Interfaces 11, 11 between the heat transfer element 10 and the thermal insulation elements 20, 30 are electrically insulated by an insulating thin membrane (resin membrane, ceramic or the like). Conduction lead wires 12, 13 are connected at the two ends of the heat transfer element 10 and with a electric power source 40.

Voltage measuring lead wires 14, 15 are connected at the two ends of the heat transfer element 10 and with a voltage measuring apparatus 50.

Conduction lead wires 21, 22 are connected with the thermal insulation element 20 and conduction lead wires 31, 32 are connected with the thermal insulation element 30. The conduction lead wires 21, 22 and 31, 32 are connected with the electric power source 40, respectively.

Numeral 60 designates a control apparatus for controlling the electric power source 40 and the voltage measuring apparatus 50. The electric power source 40, the voltage measuring apparatus 50 and the control apparatus 60 are connected by GP-IB (general purpose interface bus) control system recommended by IEEE.

Figure 2:
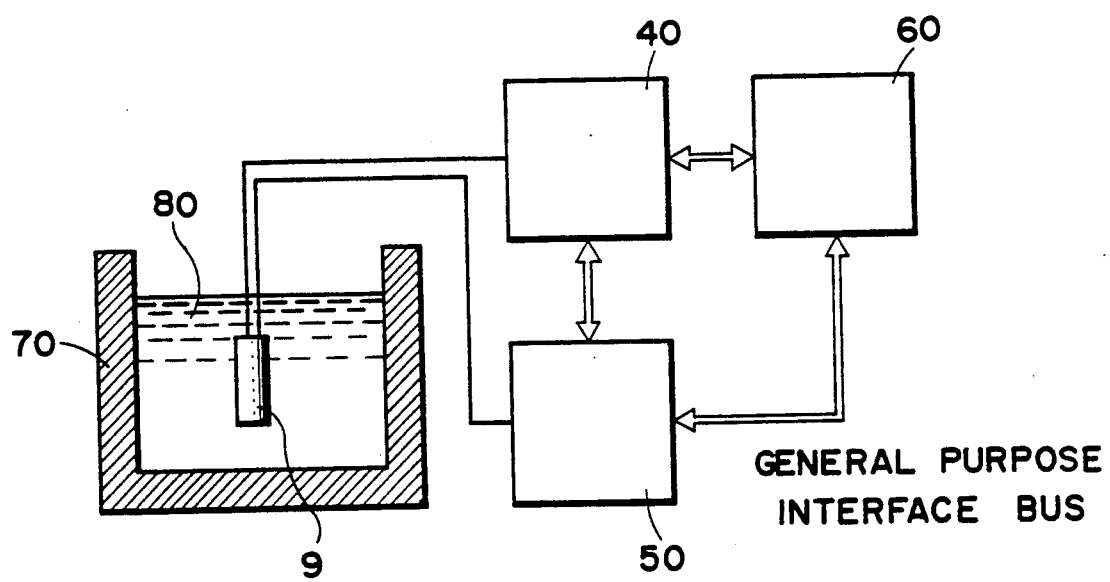
FIG. 2 is a block diagram illustrating a state in which the sensor of FIG. 1 is connected with a electric power source, a voltage measuring apparatus and a control apparatus.

As shown in FIG. 2, the sensor 9 is put into a fluid as a measuring object in a tank 70, separate currents are supplied to the heat transfer element 10 and the thermal insulation elements 20, 30, respectively, and then the temperatures of the heat transfer element 10 and the thermal insulation elements 20, 30 at the interface 11, 11 are controlled to be equal by the control apparatus 60.

A voltage applied to the heat transfer element 10 is measured by the voltage measuring apparatus 50 connected by the voltage measuring lead wire.

According to the measured voltage value and the current value applied to the heat transfer element 10, a calorific value W of the heat transfer element 10 is calculated by the aforementioned formula (1) and a heat transfer coefficient α on the boundary surface between the heat transfer element 10 and the fluid body 80 is calculated by the aforementioned formula (2).

The characteristic of the present invention will be described in reference to FIGS. 1 and 2. In the sensor 9, the heat transfer element 10 is heat-transferably contacted with the fluid 80 and the two end surfaces are not heat transferably contacted with the fluid body 80 but through interfaces form thermal insulation elements 20, 30. Since the interfaces 11, 11 have no temperature difference between the heat transfer element 10 and the thermal insulation elements 20, 30, no heat transfer between the heat transfer element 10 and the thermal insulation elements 20, 30 occurs across interfaces 11, 11.

As shown in FIG. 1, the heat capacity $W_2$ transfered through the interfaces 11, 11 becomes zero, and, thus, the heat transfer between the heat transfer element 10 and the fluid body 80 occurs only on the circumferential surface 10a of the heat transfer element 10 which is heat-transferably contacted with the fluid body 80.

Accordingly, the heat capacity transfered to the fluid body 80 through the contacting surface 10a corresponds to the entire calorific value of the heat transfer element 10. Thus, the heat capacity transfered from the heat transfer element 10 to the fluid body 80 as a measuring object can be exactly measured by using the method according to the invention.

The size of each of the parts of the sensor 9 of FIGS. 1 and 2 is optional in accordance with the usage thereof. However, for example the heat transfer element 10 is 2 mm in diameter and about 6 mm in length and the thermal insulation elements 20, 30 are 2 mm in diameter and about 2 mm in length.

In the drawings, arrows of continuous lines designate the state of thermal transfer and arrows of dotted lines designate the state of thermal insulation in which a heat cannot be transfered.

Figure 3:
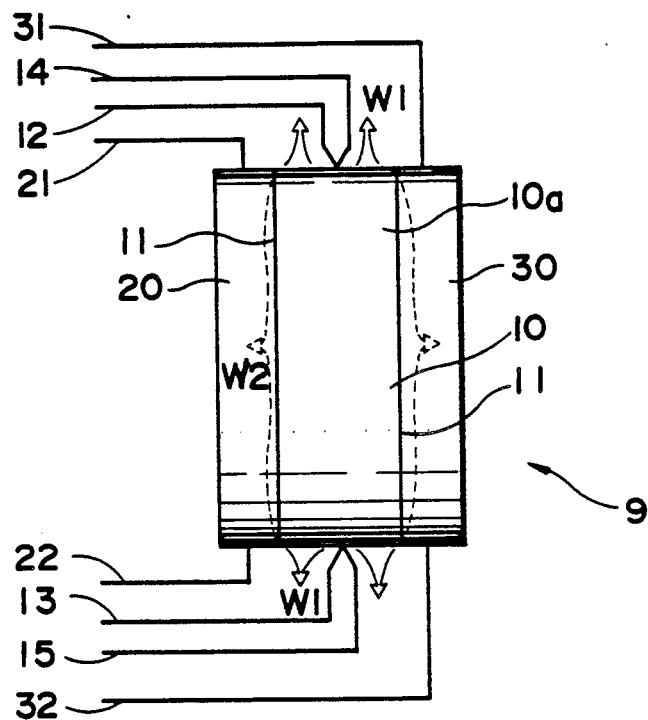
FIG. 3 is a front view illustrating an embodiment in which a combination of a heat transfer element and a thermal insulation element is in the shape of a disk.

In FIG. 3, a different embodiment in which a combination of a heat transfer element 10 and thermal insulation elements 20, 30 is in the shape of a cylindrical body, is described. In this embodiment, the thermal insulation elements 20, 30 are also interfaced at both ends of the heat transfer element 10.

The different point in wiring between the embodiment of FIG. 3 and the embodiment of FIG. 1 exists in that conduction lead wires 12, 13 and voltage measuring lead wires 14, 15 are connected with the circumferential surface 10a of the heat transfer element 10. In FIG. 1, both the lead wires are connected with both of the end surfaces of the heat transfer element 10. Other points are the same as the embodiment of FIG. 1.

In comparison with the embodiment of FIG. 1, in the embodiment of FIG. 3, further miniaturization of the sensor 9 is enabled. Namely, it provides that the heat transfer element 10 is 2 mm in diameter and 0.4 mm in thickness and the thermal insulation elements 20, 30 are 2 mm in diameter and 0.2 mm in thickness.

Figure 4:
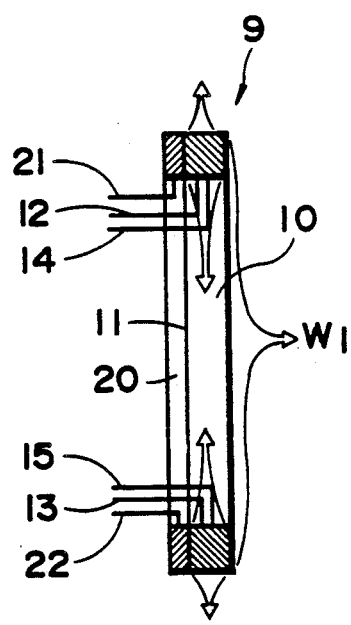
FIG. 4 is a sectional view taken as indicated by the line VI—VI of FIG. 5, illustrating an embodiment in which a combination of a heat transfer element and a thermal insulation element is in the shape of a ring.

FIG. 4 describes a further different embodiment in which a combination of a heat transfer element 10 and a thermal insulation element 20 is in the shape of a ring and the thermal insulation element 20 is interfaced at one side of the heat transfer element 10. In this embodiment, conduction lead wires 12, 13 and voltage measuring wires 14, 15 are connected with an inner circumferential surface of the heat transfer element 10 and conduction lead wire 21, 22 are connected with an inner circumference of the thermal insulation element 20.

In comparison with the other embodiments, in the embodiment of FIG. 4, since the heat transfer element 10 is in the shape of a ring, a large electrical resistance is obtained with a wider heat-transferably connecting surface of the heat transfer element 10 and therefore, measuring precision is further improved.

Figure 5:
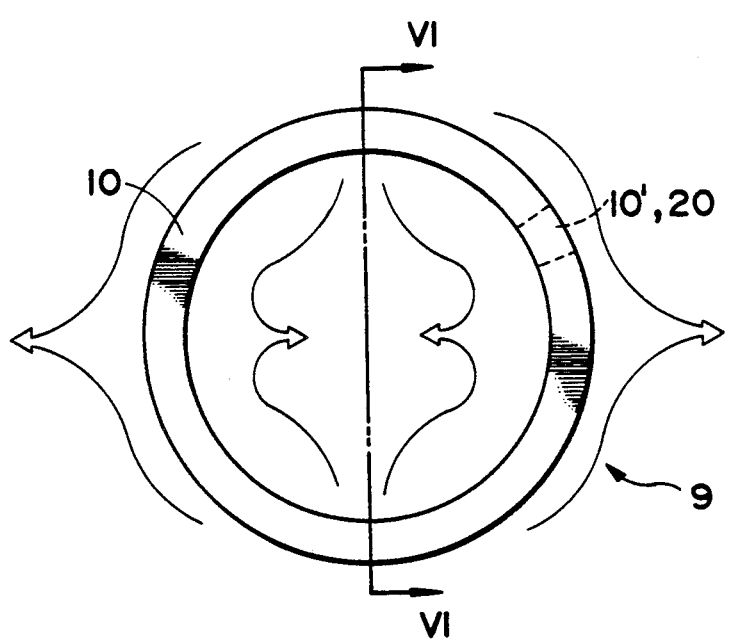
FIG. 5 is a side view illustrating an embodiment in which a notched surface is provided on a part of the circumference of the ring of FIG. 4.
Figure 6:
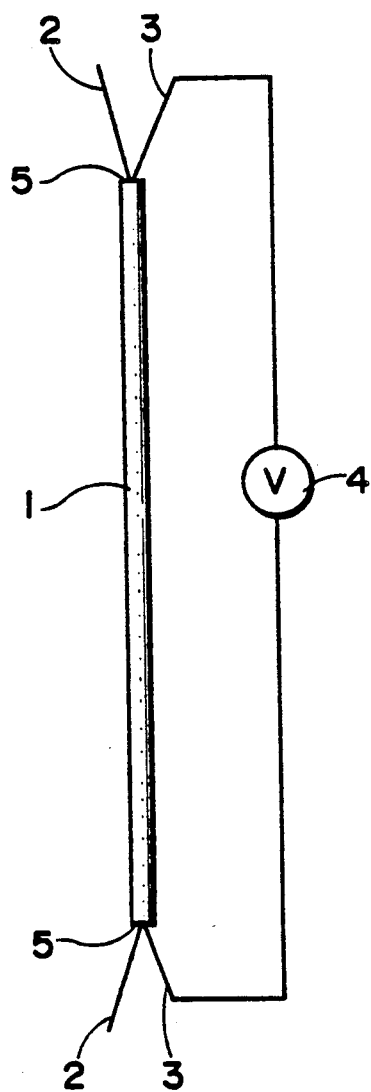
FIG. 6 is a view illustrating a traditional embodiment in which a long thin wire is used.
Figure 7:
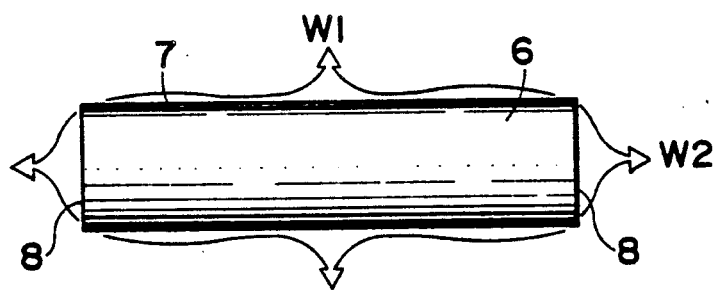
FIG. 7 is a front view illustrating the problem solved by the present invention in which a heat transfer element of a metal stick is used.

In FIG. 5, as shown by the broken line, one part of a side surface 10', 20' of the heat transfer element and the thermal insulation element of the sensor 9, in the shape of the ring described in FIG. 4, is notched. Conduction lead wires and voltage measuring wires are connected with the notched part 10', 20'. Therefore, an the electrical resistance becomes further larger and the measuring precision is further improved.

Furthermore, many additional kinds of different embodiments according to the present invention are considered as apparent to one of the art.

That is to say, the heat transfer element and the thermal insulation elements of FIG. 3 can be formed in the shape of a ring.

The one member or both the members of the heat transfer element and the thermal insulation element of FIG. 4 can be formed in the shape of a disk.

The sensor in the shape of a cylindrical body of FIG. 1 can be formed by winding a thin metal wire or a metalic paper ribbon around the sensor. All sensors can be coated with a thin non-conducting membrane.

A heat-transferably contacting surface can be optionally formed on any surface of the heat transfer element. In the embodiment of FIG. 4, the thermal insulation element can be interfaced with an outer circumferential surface or an inner circumferential surface of the heat transfer element.

As a thermal insulation element, a heating material and a vacuum insulation may be jointly used.

A heat-transferably contacting state between the heat transfer element and the thermal insulation element is not limited to be a physical contacting state.

Although particular preferred embodiments of the invention have been disclosed in detail for illustration purposes, it should be recognized that variations or modifications of the discloses embodiments including the rearrangement of parts, lie within the scope of the present invention.

What is claimed is:

1. In a method for measuring a heat transfer coefficient between a heat transfer element and a fluid body wherein a calorific value is measured by placing the heat transfer element into said fluid body and charging the heat transfer element with an electric current so as to measure said calorific value, the improvement wherein a measured calorific value is the true calorific value of the entire heat transfer element by heat-transferably contacting a particular surface of said heat transfer element with said fluid body and measuring the calorific value of that particular surface and by rendering the residual surface of said heat transfer element in a thermal insulation state.

2. A method according to claim 1 wherein the said thermal insulation state is formed by interfacing said residual surface of said heat transfer element with a heat insulation element.

3. A method according to claim 2 wherein the said thermal insulation state is formed by providing a temperature at an interface between said heat transfer element and said heat insulation element which is substantially equal to the temperature of the heat transfer element and the heat insulation element.

4. A sensor comprising a combination of a heat transfer element and a thermal insulation element wherein the said heat transfer element has a particular surface which is heat-transferably contacted with a fluid and said thermal insulation element is a residual surface of said heat transfer element, and means for holding the temperature of said thermal insulation element substantially equal to the temperature of an interface of the said heat transfer element and the said thermal insulation element such that heat cannot be transferred between said heat transfer element and said thermal insulation element.

5. A sensor according to claim 4, further wherein the means for holding the temperature of said thermal insulation element substantially equal to the temperature of said interface includes a conducting means connected with said thermal insulation element for adding heat to said thermal insulation element by means of an electrical current passing through said conducting means.

6. A sensor according to claim 4, further including a conduction means and a voltage measuring means which are connected with said heat transfer element.

7. A sensor according to claim 6, further including a control means which is connected with said conduction means and said voltage measuring means connected with said heat transfer element and conduction means connected with said thermal insulation element and said control means.

* * * * *